United States Patent
Shine

(10) Patent No.: US 6,662,043 B1
(45) Date of Patent: Dec. 9, 2003

(54) HEART BEAT COINCIDENCE DETECTION

(75) Inventor: David J. Shine, Hamden, CT (US)

(73) Assignee: GE Marquette Medical Systems, Inc., Milwaukee, WI (US)

( * ) Notice: Subject to any disclaimer, the term of this patent is extended or adjusted under 35 U.S.C. 154(b) by 229 days.

(21) Appl. No.: 09/632,271

(22) Filed: Aug. 3, 2000

(51) Int. Cl.$^7$ ................................................ A61B 5/04
(52) U.S. Cl. ...................... 600/509; 600/453; 600/511
(58) Field of Search ............................... 600/453, 483, 600/509, 511, 513, 510, 516

(56) References Cited

U.S. PATENT DOCUMENTS

| | | | |
|---|---|---|---|
| 3,827,428 A | 8/1974 | Hon et al. | 128/2.06 E |
| 4,038,536 A | 7/1977 | Feintuch | 235/152 |
| 4,211,237 A | 7/1980 | Nagel | 128/698 |
| 4,256,118 A | 3/1981 | Nagel | 128/733 |
| 4,299,234 A | 11/1981 | Epstein et al. | 128/698 |
| 4,519,396 A | 5/1985 | Epstein et al. | 128/698 |
| 4,537,200 A | 8/1985 | Widrow | 128/696 |
| 4,569,356 A | 2/1986 | Kyozuka | 128/698 |
| 4,751,931 A | 6/1988 | Briller et al. | 128/700 |
| 4,781,200 A | 11/1988 | Baker | 128/670 |
| 4,793,361 A | 12/1988 | DuFault | 128/696 |
| 4,898,179 A | 2/1990 | Sirota | 128/670 |
| 4,945,917 A | 8/1990 | Akselrod et al. | 128/696 |
| 4,984,576 A | 1/1991 | Schulenberg et al. | 128/661.07 |
| 5,042,499 A | 8/1991 | Frank et al. | 128/698 |
| 5,123,420 A | * 6/1992 | Paret | 128/698 |
| 5,289,820 A | * 3/1994 | Beach et al. | 128/661.07 |
| 5,365,933 A | * 11/1994 | Elghazzawi | 128/697 |
| 5,442,940 A | 8/1995 | Secker et al. | 128/670 |
| 5,529,073 A | 6/1996 | Kielbasiewicz | 128/696 |
| 5,724,032 A | 3/1998 | Klein et al. | 341/50 |
| 5,749,831 A | * 5/1998 | Baker | 600/301 |

FOREIGN PATENT DOCUMENTS

GB   2 220 487 A   10/1990

* cited by examiner

Primary Examiner—Jeffrey R. Jastrzab
Assistant Examiner—Frances P. Oropeza
(74) Attorney, Agent, or Firm—Foley & Lardner; Peter J. Vogel; Michael A. Della Penna

(57) ABSTRACT

A method of detecting heart beat coincidence includes receiving first and second signals from first and second heart beat sources. The method further includes detecting first heart beat occurrences on the first signal, each first heart beat occurrence having a respective time associated therewith and detecting second heart beat occurrences on the second signal, each second heart beat occurrence having a respective time associated therewith. The method further includes comparing the times of the first and second heart beat occurrences to detect coincidence.

23 Claims, 5 Drawing Sheets

HEART BEAT COINCIDENCE DETECTION

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

The present invention relates generally to medical systems and methods for monitoring a heart beat. The present invention relates more specifically to medical systems and methods for monitoring first and second heart beats and detecting coincidence.

BACKGROUND OF THE INVENTION

Medical monitoring devices are becoming increasingly important in the fields of patient diagnosis and care. New technologies give patient caregivers various alternative tools for performing the tasks necessary to address the needs of their patients.

In one example, the heartbeat of a fetus in the womb is monitored during an examination or during birth. The health and well-being of the fetus can be monitored by studying the fetal heartbeat. Transducers are positioned on or near the fetus to monitor the fetal heartbeat and are coupled with wires to a nearby computer for display and/or charting.

However, existing technology relating to transducer design and placement is prone to errors, such as, noise, multipath, and other signal disturbances. One particularly troublesome error is the tendency of the fetal transducer to acquire the heartbeat of the mother instead of the fetus. When the heartbeat of the mother is recorded and displayed as that of the fetus (e.g., on a monitor or strip chart), the caregiver risks an incorrect or inaccurate diagnosis.

Correct positioning of the fetal transducer can avoid the mother's heartbeat while acquiring the fetal heartbeat. However, it is not easy to identify when the fetal transducer is correctly positioned. One proposed solution is a fetal monitor capable of recording the heart rate traces of a fetus and a mother. The heart rates are traced on a chart and, if the heart rates are coincident, a warning signal is generated. One drawback of this proposed solution is that heart rates from two different sources can vary widely, even crossing one another at times, particularly during childbirth. Furthermore, a threshold must be established around one heart rate signal (e.g., +/−5 beats per minute) which, under some conditions, does not precisely identify whether the incorrect heart rate is being monitored.

Accordingly, what is needed is a system and method for detecting heart beat coincidence that avoids the uncertainties associated with heart rate generation and monitoring. Further, what is needed is a system and method that is more precise, and provides improved coincidence detection in a shorter time period. Further still, a system and method is needed that provides a higher degree of certainty in coincidence detection. The system and method would further be more versatile than prior systems.

BRIEF SUMMARY OF THE INVENTION

According to an exemplary embodiment, a method of detecting heart beat coincidence includes receiving first and second signals from first and second heart beat sources. The method further includes detecting first heart beat occurrences on the first signal, each first heart beat occurrence having a respective time associated therewith and detecting second heart beat occurrences on the second signal, each second heart beat occurrence having a respective time associated therewith. The method further includes comparing the times of the first and second heart beat occurrences to detect coincidence.

According to an alternative embodiment, a system for detecting heart beat coincidence includes means for receiving first and second signals from first and second heart beat sources, respectively. The system further includes means for detecting first heart beat occurrences on the first signal, each first heart beat occurrence having a respective time associated therewith and means for detecting second heart beat occurrences on the second signal, each second heart beat occurrence having a respective time associated therewith. The system further includes means for comparing the times of the first and second heart beat occurrences to detect coincidence.

According to another alternative embodiment, a heart beat coincidence detection system includes a processor and an output device. The processor is configured to receive first and second cardiac signals, to detect first and second heart beats on the first and second cardiac signals, respectively, to calculate phase shifts between respective first and second heart beats, and to generate a display signal based on the phase shifts. The output device is configured to receive the display signal and to provide the display signal to an operator.

BRIEF DESCRIPTION OF THE DRAWINGS

The invention will become more fully understood from the following detailed description, taken in conjunction with the accompanying drawings, wherein like reference numerals refer to like parts, in which.

DETAILED DESCRIPTION OF THE INVENTION

Figure 1:
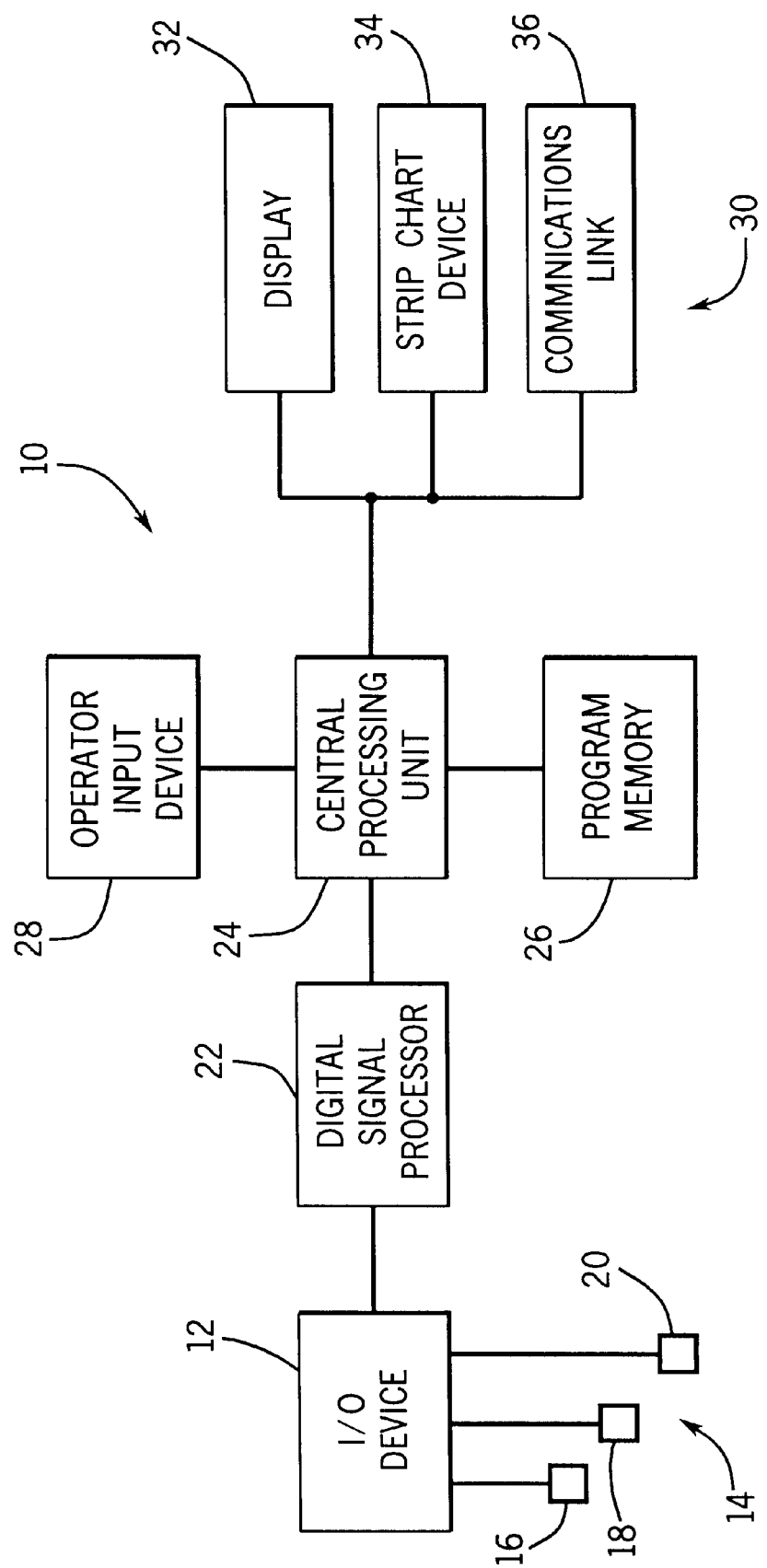
FIG. 1 is a block diagram of a heart beat coincidence detection system according to an exemplary embodiment.

Referring first to FIG. 1, a heart beat coincidence detection system 10 is shown. System 10 is implemented, for example, on a Corometrics 120 Series Maternal/Fetal Monitor manufactured by GE Marquette Medical Systems of Milwaukee, Wis. However, system 10 may be implemented on other fetal monitoring systems, or other medical devices.

System 10 includes an input/output device 12 coupleable via wires or wirelessly to one or more transducers 14. Transducers 14 include a fetal heartbeat transducer 16 and a maternal heartbeat transducer 18, and may further include additional transducers 20. Transducers 14 may each include an electrocardiogram electrode, ultrasound transducer, blood pressure transducer, pulse oximetry transducer, or other transducer configured to monitor cardiac activity from a heart beat source and to generate a cardiac signal based on that activity. Input/output device 12 includes a port, circuit board, or other circuit configured to receive the cardiac signals from transducers 14 and provide one or more of the cardiac signals to a digital signal processor 22.

Digital signal processor 22 is an integrated circuit or other circuit configured to receive analog signals from transducers 14, digitize them, and detect heart beats on the cardiac signals. Digital signal processor 22 includes a processor and program-storage memory to perform these tasks, but may include any necessary circuit elements, such as discrete components, analog components, programmable logic, etc. Digital signal processor 22 provides a priority interrupt to a central processing unit 24 (e.g., an INTEL or MOTOROLA microprocessor, or other processing circuit) each time a heart beat is detected. Central processing unit 24 runs a heart beat coincidence detection algorithm stored in program memory 26 each time the priority interrupt is received from digital signal processor 22.

The algorithm will be described below with reference to FIGS. 2A and 2B. According to an alternative structure, digital signal processor 22 and central processing unit 24 can be fabricated on one integrated circuit. Alternative methods and systems of heart beat detection for both fetal heart beats and maternal heart beats may be utilized in system 10.

System 10 further includes an operator input device 28 including keypads, switches, dials, a touch-screen interface, and/or other devices configured to receive input data from a caregiver or other operator. System 10 further includes one or more output devices 30, such as, a display 32, a strip chart device 34, and/or a communications link 36 coupled to the central processing unit 24 and including any necessary interface circuitry. Central processing unit 24 generates output signals, such as display signals, based on the heart beat coincidence detection algorithm stored in program memory 26 and provides these output signals to one or more of output devices 30.

The following is a heart beat coincidence comparison matrix.

| Mode | $F_{1ECG}$ | $F_{1US}$ | $F_{2US}$ | $M_{ECG}$ | $M_{SpO2}$ | $M_{BP}$ |
|---|---|---|---|---|---|---|
| $F_{1ECG}$ | X | YES | YES | YES | YES | NO |
| $F_{1US}$ | YES | X | YES | YES | YES | NO |
| $F_{2US}$ | YES | YES | X | YES | YES | NO |
| $M_{ECG}$ | YES | YES | YES | X | NO | NO |
| $M_{SpO2}$ | YES | YES | YES | NO | X | NO |
| $M_{BP}$ | NO | NO | NO | NO | NO | X |

Figure 2A:
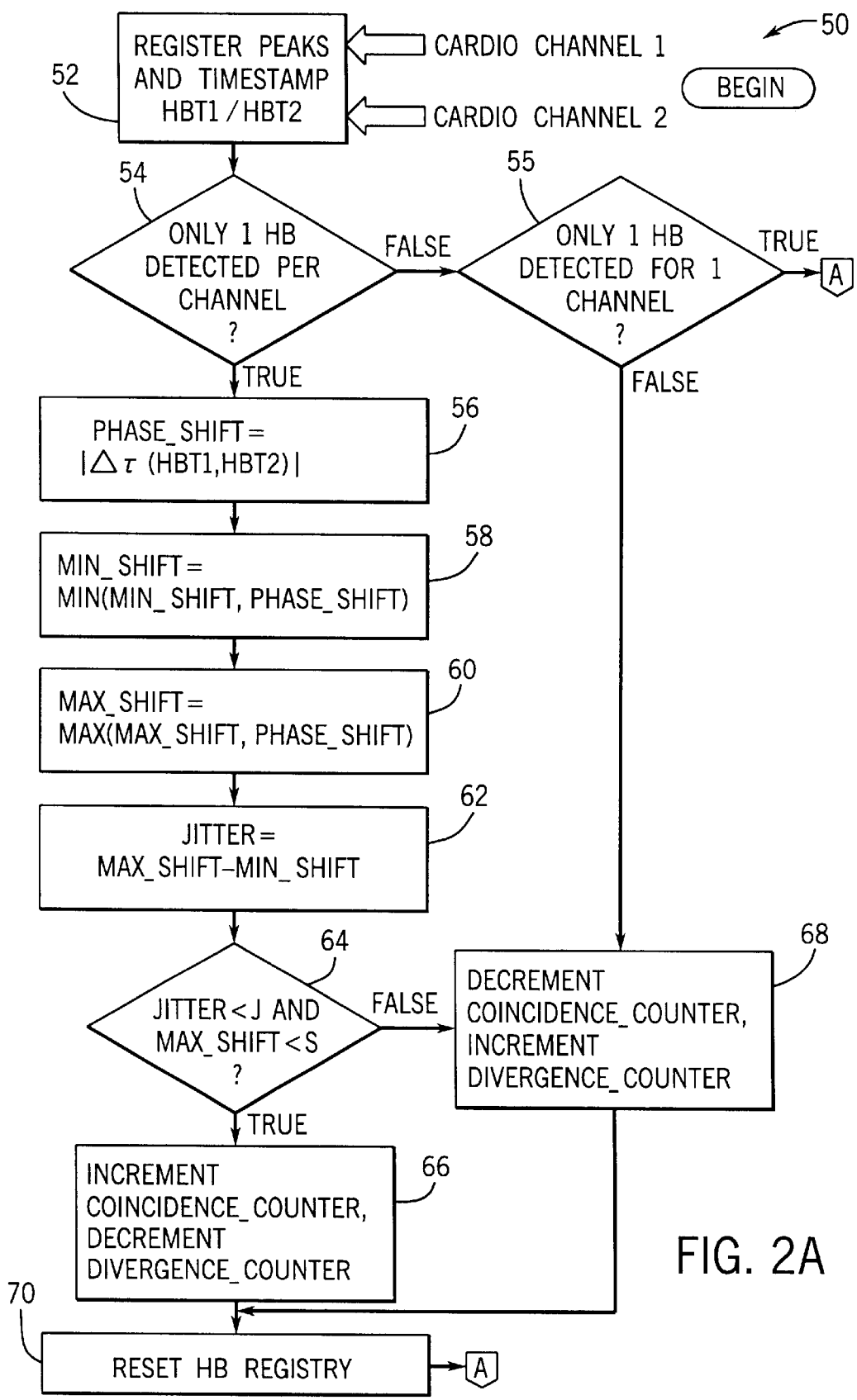
FIGS. 2A–2B are flowcharts illustrating a method of detecting heart beat coincidence according to an exemplary embodiment.
Figure 2B:
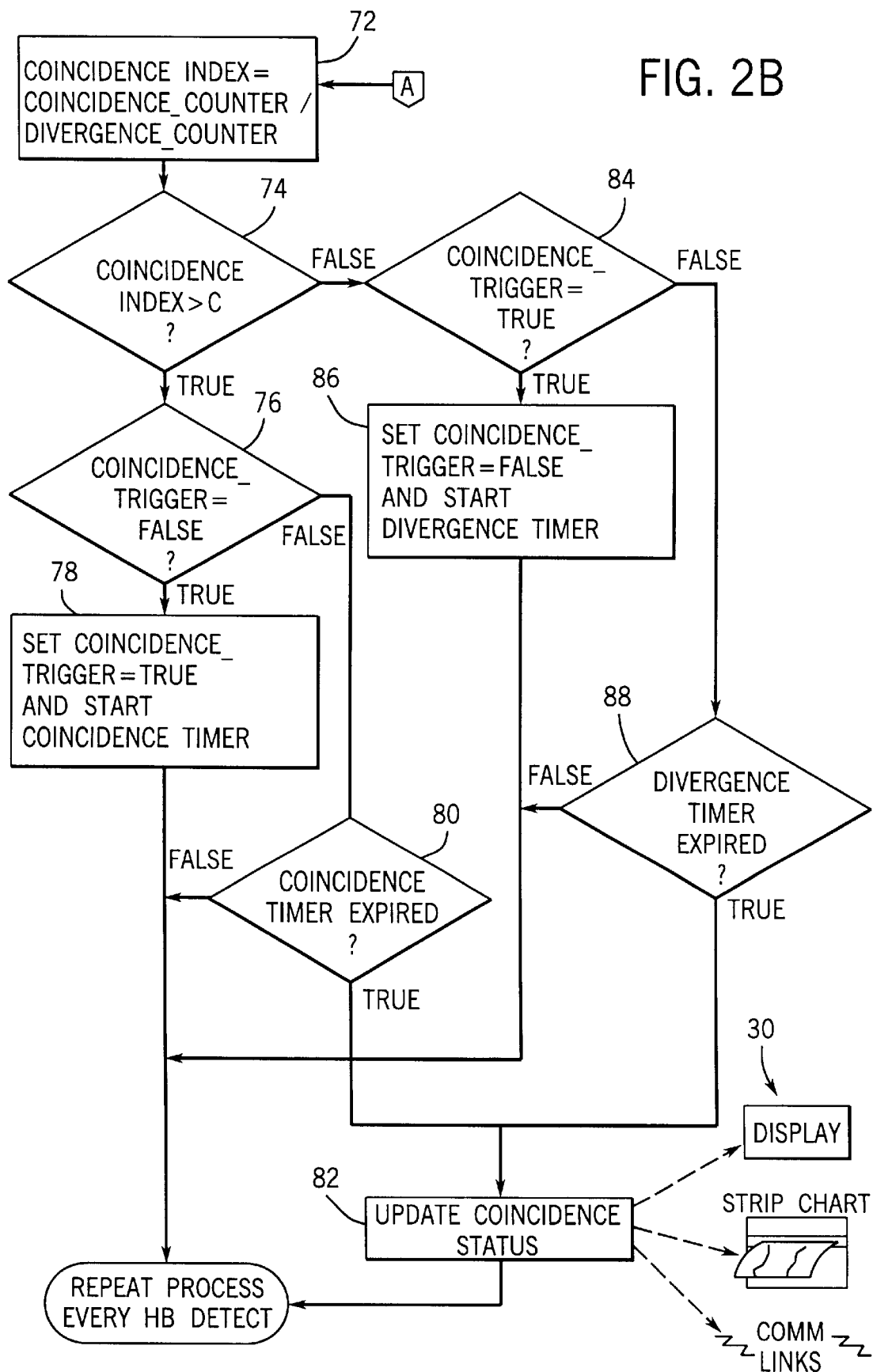

The heart beat coincidence algorithm of FIGS. 2A and 2B is configured to compare the heart beats on two or more cardiac signals and determine whether the heart beats exhibit coincidence. The above matrix illustrates the transducers which may be compared by the exemplary system and method. For example, a fetal electrocardiograph signal ($F_{1ECG}$) is compared to a maternal electrocardiograph signal ($M_{ECG}$) as indicated by the word "YES" in the chart. However, a fetal electrocardiograph signal ($F_{1ECG}$) is not compared to a maternal blood pressure signal ($M_{BP}$) as indicated by the word "NO" in the chart. The symbols $F_{1ECG}$, $F_{1US}$ (fetal ultrasound signal 1), $F_{2US}$ (fetal ultrasound signal 2), $M_{ECG}$, $M_{SpO2}$ (maternal pulse oximetry transducer), and $M_{BP}$ correspond to ports of input/output device 12 configured to receive cardiac signals from corresponding transducers. Thus, $F_{1ECG}$ is not compared to $F_{1ECG}$ as indicated by the "X" since only one port on system 10 is available for this transducer. Further, it is noted that the maternal blood pressure sensor is not utilized in this exemplary embodiment for comparison to any other signal. Other alternative configurations of this matrix are contemplated, depending on the capabilities of the system.

Referring now to FIGS. 2A and 2B, an exemplary heart beat coincidence detection method 50 is shown. Method 50 is operable in system 10 as software, but may alternatively be operable via discrete circuit elements or other programming elements. At step 52, cardiac signals on two channels, channel 1 and channel 2, are monitored. When a heart beat occurrence is detected on one of channels 1 or 2, the heart beat occurrence is registered and timestamped. HBT1 and HBT2 in FIG. 2A indicate the heart beat timestamps for a heart beat occurrence detected on channel 1 and a heart beat occurrence detected on channel 2, respectively. When a heart beat occurrence is detected on the other of the two channels, the method proceeds to step 54. A heart beat occurrence on one of channels 1 and 2 followed by a heart beat occurrence on the other of channels 1 and 2 is referred to hereinafter as a cycle.

At step 54, the method identifies whether the heart beat occurrences on channels 1 and 2 bear a 1:1 correspondence. In other words, at step 54, the method calculates whether the number of heart beat occurrences from one of channels 1 and 2 occurs twice between successive heart beat occurrences in the other channel. If a correspondence of greater or less than 1:1 is found, the method proceeds to step 55. At step 55, if channel 1 (representing the fetal heart beat in this exemplary embodiment) has greater than one heart beat for one heart beat of channel 2 (representing the maternal heart beat in this exemplary embodiment), the method proceeds to step 68. If channel 1 has less than one heart beat for one heart beat of channel 2, the method proceeds to step 72 (FIG. 2B). Alternatively, when the heart beat occurrences indicate greater or less than 1:1 correspondence, the method may directly generate a divergence signal, as described below with respect to step 82.

Once a cycle of heart beat occurrences is detected and time stamped, times associated with each heart beat occurrence are compared to detect coincidence. The following is one exemplary method for comparing heart beat occurrences to detect coincidence, though alternative methods are contemplated utilizing heart beat occurrences. At step 56, a time offset (e.g., a phase shift) between HBT1 and HBT2 is calculated. Next, the running jitter between multiple cycles of occurrences is determined to indicate coincidence or divergence.

In this exemplary embodiment, determining jitter between cycles includes keeping a record of the minimum and maximum phase shifts occurring among a plurality of cycles. Therefore, the jitter determination assumes multiple cycles over a period of time (e.g., a time "window"). The time window is a fixed time (e.g., three seconds) in this exemplary embodiment after which the minimum and maximum phase shift variables are reset but may alternatively depend on a cycle count or all cycles during a period of 1:1 correspondence.

At step 58, a minimum phase shift variable is updated with the new phase shift provided the new phase shift is smaller than the prior minimum phase shift. At step 60, a maximum phase shift variable is updated with the new phase shift provided the new phase shift is greater than the prior maximum phase shift. At step 62, a jitter is calculated by subtracting the minimum phase shift from the maximum phase shift.

Once the phase relationship has been characterized by phase shift and jitter, this data is used to determine if the heart beat occurrences are representative of coincidence or divergence. Maximum jitter and maximum phase shift criteria are applied. Thus, at step 64, the jitter is compared to a maximum jitter threshold (J) and the maximum phase shift is compared to a maximum phase shift threshold (S). Maximum jitter threshold (J) and maximum phase shift threshold (S) are variable and may be adjusted to tune the algorithm. For example, maximum jitter threshold (J) may be set at approximately 100 ms, or as low as approximately 1 ms. In one exemplary embodiment, maximum jitter threshold (J) is less than one-half the minimum expected beat-to-beat interval. For example, if the minimum expected beat-to-beat interval is 200 ms (i.e., corresponding to 300 beats per minute), maximum jitter threshold (J) is set to one-half of 200 ms, or 100 ms. Phase shift threshold (S) may be set at approximately 200 ms, or between 1 and 2,000 ms. Alternatively, (J) and (S) may be tuned to any value, depending upon the application and such factors as transducer type/cardiac source.

Maximum phase shift and maximum phase jitter thresholds may be dynamically variable by the algorithm or static. The potential range of the phase shift between channels with signal peaks demonstrating a 1:1 correspondence is defined as 0–359 degrees, but would generally be expected to be within 180 degrees. In the time domain this could be from 0 to 1999 milliseconds depending upon the period between beats from channel 1 and channel 2. Coinciding heart beats at the low end could occur offset 1999 milliseconds from one another and be 359 degrees out of phase.

Maximum phase jitter may be defined as a constant or as a variable to the algorithm. One method is to make J a function of the maximum phase shift. For example, J=max shift/3. In this example, the maximum allowable jitter for beats to be characterized as coinciding would be 33%.

An embodiment that followed these principles would, first, characterize beats from two channels to be within 359 degrees phase of each other if the beat registry is 1:1. Then, within a window of comparison, the jitter, which is evaluated as the difference between the maximum and minimum phase shift, may be qualified characteristic of coincidence if less than 33% of the maximum. Maximum shift may be further qualified in the time domain if so desired, and would be a function which takes into account system latencies, This embodiment is more forgiving of the degree of phase shift, but enforces consistency in the phase relationship by allowing only a minimum in the phase jitter. With this approach the max jitter threshold should not be implemented to exceed 49%.

If the jitter is less than the maximum jitter threshold and the maximum phase shift is less than the maximum phase shift threshold, a coincidence counter is incremented and a divergence counter is decremented at step 66. Alternatively, the coincidence counter is decremented and the divergence counter is incremented at step 68. As indicated by steps 64, 66, and 68, both an increasing jitter and an exceedingly high phase shift indicate divergence. A steady jitter and a smaller phase shift indicate coincidence.

At step 70 the heart beat registry is reset and prepared for registration of a new cycle of heart beat occurrences.

At step 72, a coincidence index is calculated. The coincidence index represents the degree of coincidence or divergence between heart beat occurrences on channels 1 and 2 over a time window which is either fixed or variable, as described hereinabove. In this example, the time window includes all heart beat occurrences in a three second window. The time window may include between 2 and 100 heart beat cycles. At step 72, the coincidence index may be calculated, for example, as a ratio (as in this exemplary embodiment) or as a percentage of cycles which coincide.

At step 74, the coincidence index is compared to coincidence/divergence criteria (e.g., a coincidence trigger threshold (C)) which indicates when a sufficient amount of coincidence or divergence is detected to alert the operator. The coincidence/divergence criteria are variable and may be adjusted to tune the algorithm. For example, coincidence trigger threshold (C) may be set at approximately 70% of cycles being coincident, or approximately 3 coincident cycles to every 1 divergent cycle. Alternatively, (C) may range between 50% and 90%, or may be any other value, depending upon the application and such factors as transducer type/cardiac source.

If the coincidence index meets the coincidence/divergence criteria, a timer is started for the respective criterion. If the coincidence index continues to meet the coincidence/divergence criteria over multiple heart beat cycles for a predetermined time period, a signal will be generated to the user to notify the user of coincidence or divergence. In this exemplary embodiment, a coincidence trigger flag is used to implement the timer. At step 74, if the coincidence index exceeds the coincidence trigger threshold (C), the coincidence trigger flag is checked at step 76 to see if it is FALSE. If the coincidence trigger flag is FALSE, at step 78 the coincidence trigger flag is set to TRUE, a coincidence timer is started, and the algorithm returns to step 52. The coincidence timer may be set to 60 seconds, between 40 and 80 seconds, or any other time, depending upon the application. If the coincidence trigger flag is not FALSE at step 76, at step 80 the coincidence timer is checked to see if it expired. If not, the algorithm returns to step 52. If so, a coincidence signal is generated at step 82 and provided to one of output devices 30.

Returning to step 74, if the coincidence index does not exceed the coincidence index trigger threshold (C), the coincidence trigger flag is checked at step 84. If the coincidence trigger flag is TRUE, at step 86, the coincidence trigger flag is set to FALSE, a divergence timer is started, and the algorithm returns to step 52. The divergence timer may be set to 5 seconds, between 1 and 10 seconds, or any other time, depending upon the application. If the coincidence trigger flag is not TRUE, at step 88 the divergence timer is checked to see if it expired. If not, the algorithm returns to step 52. If so, a divergence signal is generated at step 82 and provided to one of output devices 30.

In operation, when the coincidence index exceeds coincidence index trigger threshold (C) for a predetermined time (i.e., the duration of the coincidence timer), a coincidence indicia is generated on one or more of output devices 30. When the coincidence index is below coincidence index trigger threshold (C) for a predetermined time (i.e., the duration of the divergence timer), a divergence indicia is generated on one or more of output devices 30. According to one alternative, a divergence indicia is only provided to output devices 30 if a coincidence indicia was previously provided to output devices 30. This alternative is particularly advantageous when the strip chart is utilized, since no indicia need be provided to the user when the heart beat occurrences are divergent unless a previous indicia indicated the heart beat occurrences were coincident.

Figure 3:
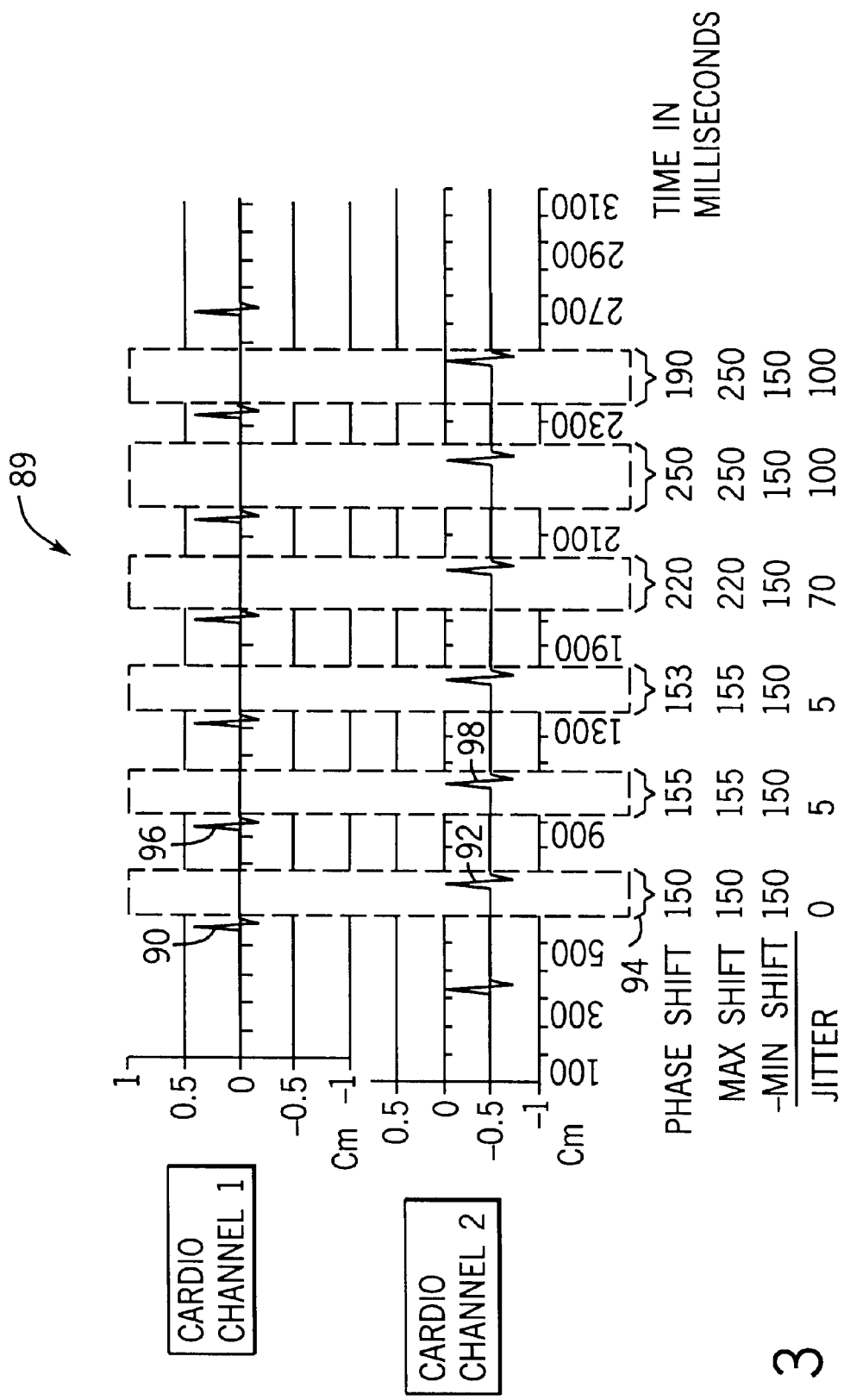
FIG. 3 is a graph illustrating several steps of the method of FIG. 2A.

Referring now to FIG. 3, a chart 89 illustrates the operation of a portion of the heart beat coincidence detection algorithm of FIG. 2A. A heart beat occurrence on channel 1 is shown at occurrence 90. A heart beat occurrence on channel 2 is shown at occurrence 92. The phase shift or time offset between occurrences 90 and 92 is indicated by time period 94. The X-axis of the chart represents real time in milliseconds (ms). In this example, the phase shift between occurrence 90 and 92 is 150 ms, as shown.

In operation, the algorithm first updates the maximum and minimum phase shift values with the new phase shift value of 150 ms. A subsequent heart beat occurrence 96 is received on channel 1, and a further subsequent heart beat occurrence 98 is received on channel 2. Note that 1:1 correspondence is maintained between heart beat occurrences on channels 1 and 2 from the first cycle to the second cycle. The phase shift between occurrences 96 and 98 is calculated as 155 ms, indicating a slight difference from the previous cycle. The maximum phase shift is updated to equal 155 ms and a jitter is calculated as 5 ms. Further heart beat occurrences on chart 89 indicate phase shifts of 153 ms, 220 ms, 250 ms, and 190 ms and corresponding jitters of 5 milliseconds, 70 milliseconds, 100 milliseconds, and 100 milliseconds.

The maximum phase shift and jitter are compared to maximum phase shift threshold (S) and maximum jitter threshold (J) to determine whether coincidence and divergence counters should be incremented or decremented. The coincidence index is then calculated and compared to the coincidence index trigger threshold (C). This occurs over a three second time window. Processing continues in accordance with the relevant steps of FIG. 2B. The output of the algorithm is dependent on the values of thresholds (J), (S), and (C), which may be programmed when manufactured, may be updateable, and may also be adjusted by the operator via operator input device 28 to give the operator control over the sensitivity.

Figure 4:
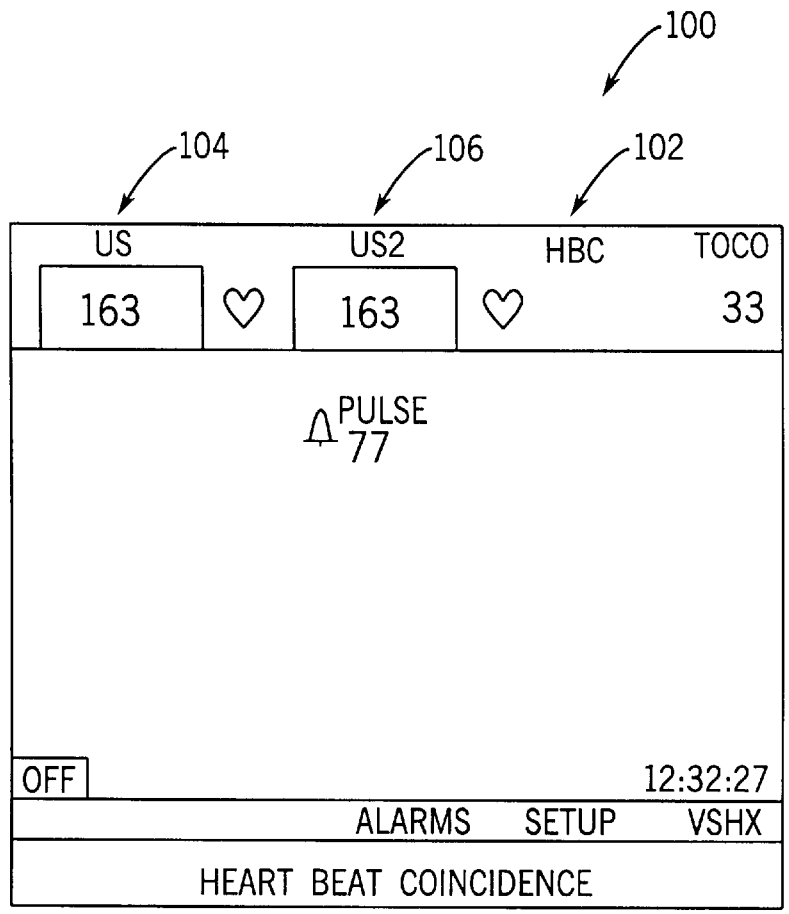
FIG. 4 is a screen display providing coincidence status according to an exemplary embodiment.

Referring now to FIG. 4, a screen display 100 is shown. Screen display 100 is generated by display 32 (FIG. 1) in response to display signals provided by central processing unit 24. Additional graphics cards or alternative circuitry may be implemented. Screen display 100 includes an indicia 102 (e.g., the text "HBC") indicating that the heart beat coincidence feature is currently operational. At step 82 of the heart beat coincidence algorithm (FIG. 2B), the algorithm generates a display signal which is one of a coincidence signal, a divergence signal, or no signal. Display 100 indicates that a coincidence signal is received by displaying heart rates for channels 1 and 2 in inverse video at indicia 104 and 106. Other indicia may be used to indicate coincidence, such as, two side-by-side hearts, the text "COINCIDENCE DETECTED", an audible tone, other indicia, or some combination thereof. Divergence is indicated in this example by ordinary (i.e., non-inverse) video, but may be indicated by a different indicia or by no indicia.

Figure 5:
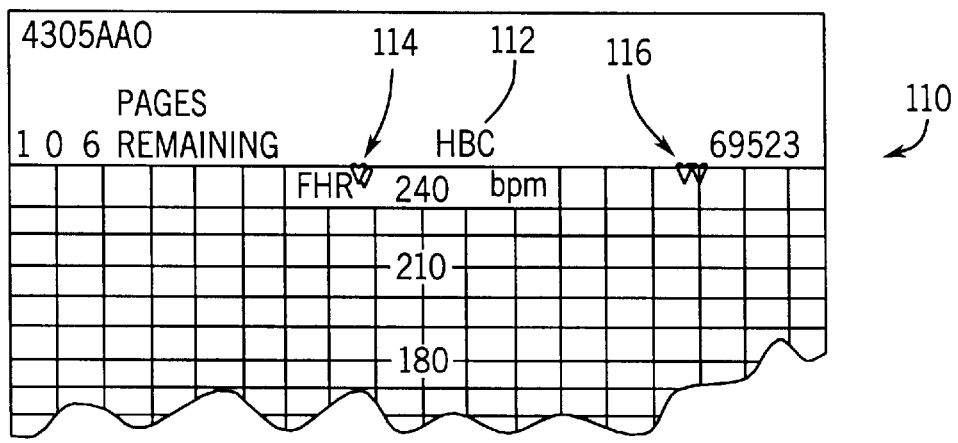
FIG. 5 is a portion of a strip chart providing coincidence status according to an exemplary embodiment.

Referring now to FIG. 5, a portion 110 of a strip chart is shown. Portion 110 is generated by strip chart device 34 (FIG. 1) in response to signals provided by central processing unit 24. Additional graphics cards or alternative circuitry may be implemented. Portion 110 includes an indicia 112 (e.g., the text "HBC") indicating that the heart beat coincidence feature is currently operational. Indicia 112 is printed periodically (e.g., every 30 minutes), but may alternatively be printed only once. At step 82 of the heart beat coincidence algorithm (FIG. 2B), the algorithm generates a display signal which is one of a coincidence signal and a divergence signal. Strip chart device 34 indicates that a coincidence signal is received by printing a coincidence indicia 114 (e.g., two overlapping heart icons). Other indicia may be used, such as, the text "COINCIDENCE DETECTED", an audible tone, or some combination thereof. Divergence may be indicated by a different indicia, such as indicia 116 (e.g., two non-overlapping heart icons) or by no indicia. Indicia 116 indicates that the coincidence was resolved. Coincidence indicia 114 and divergence indicia 116 may be printed periodically to approve the current status, or may be printed only when the status changes.

According to a further advantageous feature, the coincidence or divergence status may also be output via communications link 36.

While the embodiments and application of the invention illustrated in the figures and described above are presently preferred, it should be understood that these embodiments are offered by way of example only. For example, alternative algorithms may be employed to compare the heart beat occurrences. Further, the method steps presented may be employed in a different order. Accordingly, the present invention is not limited to a particular embodiment, but extends to various modifications that nevertheless fall within the scope of the appended claims.

What is claimed is:

1. A method of detecting heart beat coincidence, comprising:
receiving first and second signals from first and second heart beat sources, respectively;
detecting first heart beat occurrences on the first signal, each first heart beat occurrence having a respective time associated therewith;
detecting second heart beat occurrences on the second signal, each second heart beat occurrence having a respective time associated therewith; and
comparing the times of the first and second heart beat occurrences to detect coincidence including calculating a plurality of time offsets between the first and second heart beat occurrences and calculating a jitter between a first time offset and a second time offset.

2. A method of detecting heart beat coincidence, comprising:
receiving first and second signals from first and second heat beat sources, respectively;
detecting first heart beat occurrences on the first signal, each first heart beat occurrence having a respective time associated therewith;
detecting second heart beat occurrences on the second signal, each second heart beat occurrence having a respective time associated therewith;
comparing the times of the first and second heart beat occurrences to detect coincidence including calculating the number of second heart beat occurrences occurring between two first heart beat occurrences; and
generating a divergence signal when a plurality of second heart beat occurrences occur between the two first heart beat occurrences.

3. The method of claim 1, further comprising generating one of a coincidence signal and a divergence signal based on the plurality of time offsets.

4. The method of claim 3, wherein the plurality of time offsets are defined by a time window.

5. The method of claim 1, wherein the step of comparing includes comparing the jitter to a predetermined jitter value and incrementing a coincidence counter when the jitter is less than the predetermined jitter value.

6. A method of detecting heat beat coincidence, comprising:
receiving first and second signals from first and second heat beat sources, respectively;

detecting first heart beat occurrences on the first signal, each first heart beat occurrence having a respective time associated therewith;

detecting second heat beat occurrences on the second signal, each second heart beat occurrence having a respective time associated therewith;

comparing the times of the first and second heart beat occurrences to detect coincidence, including:

calculating a plurality of time offsets between the first and second heart beat occurrences;

calculating a jitter between a first time offset and a second time offset;

comparing the jitter to a predetermined jitter value and incrementing a coincidence counter when the jitter is less than a predetermined jitter value;

incrementing a divergence counter when the jitter is greater than the predetermined jitter value; and calculating a coincidence index based on the ratio of the coincidence counter to the divergence counter; and generating one of a coincidence signal and a divergence signal based on a plurality of time offsets.

7. The method of claim 6, wherein the step of generating includes generating the coincidence signal when the coincidence index exceeds a predetermined coincidence index value.

8. The method of claim 7, wherein the coincident signal is generated only when the coincidence index exceeds the predetermined coincidence index value for a predetermined time.

9. The method of claim 7, further comprising generating the divergence signal when the coincidence index is less than the predetermined coincidence index value.

10. The method of claim 9, wherein the divergence signal is generated only when the coincidence index is less than the predetermined coincidence index value for a predetermined time.

11. The method of claim 1, wherein the step of comparing occurs in response to the detection of a heart beat occurrence on either of the first and second signals.

12. The method of claim 3, further comprising:

updating a maximum time offset variable after each of the plurality of time offsets is calculated;

comparing the maximum time offset variable to a predetermined threshold; and generating the one of the coincidence signal and the divergence signal based on this comparison.

13. The method of claim 5, wherein the step of comparing includes incrementing a divergence counter when the jitter is greater than the predetermined jitter value and calculating a coincidence index based on a percentage of divergent cycles to non-divergent cycles.

14. A system for detecting heart beat coincidence, comprising:

means for receiving first and second signals from first and second heart beat sources, respectively;

means for detecting first heart beat occurrences on the first signal, each first heart beat occurrence having a respective time associated therewith;

means for detecting second heart beat occurrences on the second signal, each second heart beat occurrence having a respective time associated therewith; and means for comparing the times of the first and second heart beat occurrences to detect coincidence including means for calculating a plurality of time offsets between the first and second heat beat occurrences and means for calculating a jitter between a first time offset and a second time offset.

15. A system for detecting heart beat coincidence, comprising:

means for receiving first and second signals from first and second heart beat sources, respectively;

means for detecting first heart beat occurrences on the first signal, each first heart beat occurrence having a respective time associated therewith;

means for detecting second heart beat occurrences on the second signal, each second heart beat occurrence having a respective time associated therewith; and means for comparing the times of the first and second heart beat occurrences to detect coincidence including means for calculating the number of second heart beat occurrences occurring between two first heart beat occurrences; and means for generating a divergence signal when a plurality of second heart beat occurrences occur between the two first heart beat occurrences.

16. The system of claim 14, further comprising means for generating one of a coincidence signal and a divergence signal based on the plurality of time offsets.

17. The system of claim 14, wherein the means for comparing occurs in response to the detection of a heart beat occurrence on either of the first and second signals.

18. A heart beat coincidence detection system, comprising:

a processor configured to receive first and second cardiac signals, to detect first and second heart beats on the first and second cardiac signals, respectively, to calculate phase shifts between respective first and second heart beats, and to generate a display signal based on the phase shifts; and an output device configured to receive the display signal and to provide the display signal to an operator;

wherein the processor is configured to calculate a jitter based on the phase shifts.

19. The heart beat coincidence detection system of claim 18, wherein the processor includes a digital signal processor configured to receive the first and second cardiac signals and to detect the first and second heart beats on the first and second cardiac signals.

20. The heart beat coincidence detection system of claim 18, wherein the output device is a communications link.

21. The heart beat coincidence detection system of claim 18, further comprising an input/output device coupled to the processor configured to receive the first and second cardiac signals and to provide the first and second cardiac signals to the processor.

22. The heart beat coincidence detection system of claim 18, wherein the processor is configured to compare the jitter to a jitter threshold, and to generate the display signal based on the comparison.

23. The heart beat coincidence detection system of claim 18, wherein the processor is configured to calculate a maximum phase shift based on the phase shifts, to compare the maximum phase shift to a maximum phase shift threshold, and to generate the display signal based on the comparison.

* * * * *

UNITED STATES PATENT AND TRADEMARK OFFICE
CERTIFICATE OF CORRECTION

PATENT NO. : 6,662,043 B1
DATED : December 9, 2003
INVENTOR(S) : David J. Shine

It is certified that error appears in the above-identified patent and that said Letters Patent is hereby corrected as shown below:

Column 8,
Lines 40, 63 and 66, replace "heat" with -- heart --.

Column 9,
Line 4, replace "heat" with -- heart --.

Column 10,
Line 2, replace "heat" with -- heart --.

Signed and Sealed this

Twentieth Day of April, 2004

JON W. DUDAS
*Acting Director of the United States Patent and Trademark Office*